(12) United States Patent
Carter

(10) Patent No.: US 7,998,066 B2
(45) Date of Patent: Aug. 16, 2011

(54) EVACUATION CHAMBER

(75) Inventor: Frank C. Carter, Wormleysburg, PA (US)

(73) Assignee: Chek-Med Systems, Inc., Camp Hill, PA (US)

( * ) Notice: Subject to any disclaimer, the term of this patent is extended or adjusted under 35 U.S.C. 154(b) by 579 days.

(21) Appl. No.: 12/284,824

(22) Filed: Sep. 25, 2008

(65) Prior Publication Data

US 2010/0076420 A1  Mar. 25, 2010

(51) Int. Cl.
*A61B 1/12* (2006.01)
*A61B 18/18* (2006.01)

(52) U.S. Cl. ............. 600/156; 606/20; 606/21; 606/22; 606/23; 604/902

(58) Field of Classification Search .................. 604/319, 604/523, 533, 539, 902; 600/156; 606/20–23
See application file for complete search history.

(56) References Cited

U.S. PATENT DOCUMENTS

| | | | |
|---|---|---|---|
| 5,562,640 A | 10/1996 | McCabe et al. | |
| 5,688,256 A | 11/1997 | Surratt et al. | |
| 5,846,235 A | 12/1998 | Pasricha et al. | |
| 6,849,042 B2 * | 2/2005 | Christopher | 600/156 |
| 2004/0186467 A1 * | 9/2004 | Swanson et al. | 606/41 |

* cited by examiner

*Primary Examiner* — Nicholas D Lucchesi
*Assistant Examiner* — Leah Stohr
(74) *Attorney, Agent, or Firm* — Eugene Chovanes

(57) ABSTRACT

During cryotherapy, using an endoscope that extends within a patient to a cold treatment site, the device of the invention vacuums gas from the site through radial intake ports to a cylindrical space in an evacuation chamber held elastically circumferentially about the distal end of the endoscope tube that carries the cryoprobe to the site.

5 Claims, 3 Drawing Sheets

EVACUATION CHAMBER

BACKGROUND OF THE INVENTION (1) Field of the Invention

This invention relates to cryotherapy, or the use of extreme cold in medical treatment, based on the principle that short applications of such extreme cold can produce localized tissue destruction.

(2) Description of Related Art

This invention is used with an endoscope that places, within a patient, the cryoprobe instrument disclosed in U.S. Pat. No. 5,846,235, for Endoscopic Cryospray Device, incorporated herein by reference. Liquid under pressure passes through the cryoprobe to a site within a patient, for medical treatment. At the site, the liquid refrigerant is sprayed from a nozzle and expands into a gas, producing extreme cold, through the Joule-Thompson effect.

BRIEF SUMMARY OF THE INVENTION

The present invention is used to evacuate gas created at the cold treatment site during cryotherapy. An evacuation chamber in the device is secured to the distal end of the endoscope tube that places the cryoprobe of the '235 patent, at the cold treatment site, where a liquid under pressure is sprayed from the end of the cryoprobe tube at the treatment site, and the liquid evaporates into a gas.

The evacuation chamber does not interfere with the view of the cold treatment site being transmitted by the endoscope to the operator, nor does the evacuation chamber interfere with the operations at the cold treatment site.

The evacuation chamber, which is secured elastically circumferentially around the distal end of the endoscopic tube, vacuums the gases indirectly through radially extending ports, into a cylindrical space, from the cold treatment site. The evacuation chamber, which is of rubber or other elastic material, can be adjusted longitudinally on the endoscope tube, near the distal end, at a location deemed optimum by the operator, so that the evacuation chamber is close to the cold treatment site to vacuum the gases, but not so close that it interferes with operations at the cold treatment site.

A flat evacuation tube extending along the endoscope tube, leads away from the evacuation chamber, to carry the gases outside the patient.

DETAILED DESCRIPTION OF THE INVENTION

Figure 1:
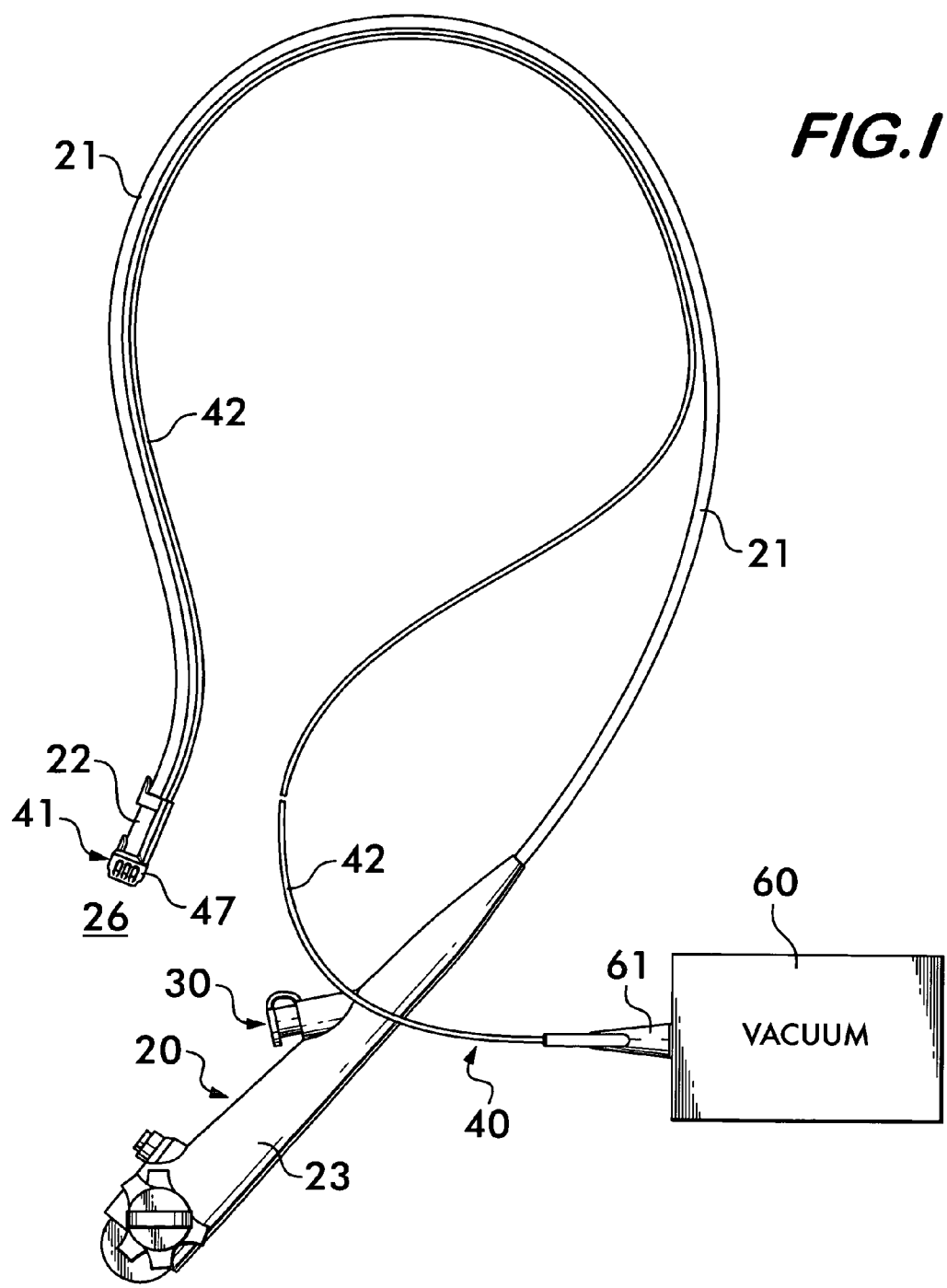
FIG. 1 is a schematic view of an endoscope, with the evacuation device of the invention attached.

There is shown in FIG. 1 a conventional prior art endoscope 20 having an endoscope tube 21, a distal end 22, and controls 23.

A cryoprobe, as shown in the '235 patent, is intended to be inserted through port 30 into endoscope tube 21 to a cold treatment site 26 within a patient for medical treatment. A refrigerant under pressure, as disclosed in the '235 patent is sprayed at the cold treatment site 26 through the spray nozzle of the cryoprobe, as seen in the '235 patent.

As explained in the '235 patent, the cryoprobe permits the delivery of liquid under pressure, in the form of a spray, to the cold treatment site 26 within the patient. The spray instantly transforms from a liquid into a gas, creating an extremely cold environment at the cold treatment site 26 through the Joule-Thompson effect, as explained in the '235 patent.

The cryoprobe is inserted through port 30 in the endoscope, as seen in FIG. 1.

As seen in the '235 patent, the cryoprobe includes an elongated, flexible tube having a fluid passage defined therethrough; a proximal connector portion provided at the proximal end of the tube for coupling the tube to a pressurized source of cryogenic refrigerant; and a nozzle tip mounted on the distal end of the tube. The nozzle tip has an outlet orifice constructed and arranged such that through the Joule-Thompson effect, cryogenic refrigerant exiting through the outlet orifice expansion chamber rapidly and substantially expands and cools, rapidly vaporizing and expanding several hundred-fold in volume.

The invention can also be used to remove gas at a cold treatment site within a patient, wherein the cold environment is created by a cold refrigerant such as cold liquid nitrogen itself. Such a cold refrigerant does not depend on the Joule-Thompson effect. The cold liquid does however evaporate, or boil, into a gas at the cold treatment site. The gas is then removed by the evacuation device of the invention.

It is necessary to evacuate this gas, in order to keep the cold treatment site 26 view clear to the operator at the distal end 22 of the endoscope tube 21, to avoid interference with the cryogenic spray being applied at the treatment site 26, and to avoid a gas pressure build-up within the patient.

The gas evacuation device 40 of the invention comprising an evacuation chamber 41 and flat evacuation tube 42 is secured to the outside of the endoscope tube 21. The endoscope tube 21 contains at its distal end 22 the cryoprobe spray nozzle illustrated in the '235 patent, through which the cryogenic refrigerant is sprayed at the cold treatment site 26. When the spray nozzle is positioned at the treatment site by the endoscope 20, the evacuation chamber 41 is simultaneously positioned adjacent the cold treatment site 26.

Figure 2:
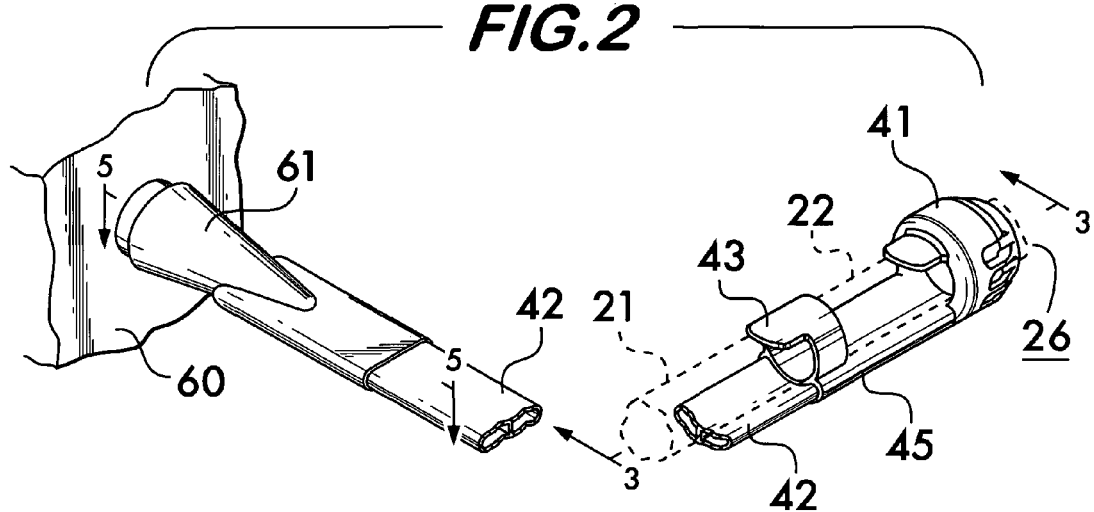
FIG. 2 is a schematic perspective view of the ends of the evacuation tube with the middle portion of the tube broken away, and with evacuation chamber attached to the distal end of the evacuation tube, and the proximate end of the evacuation tube connected to a vacuum pump.
Figure 3:
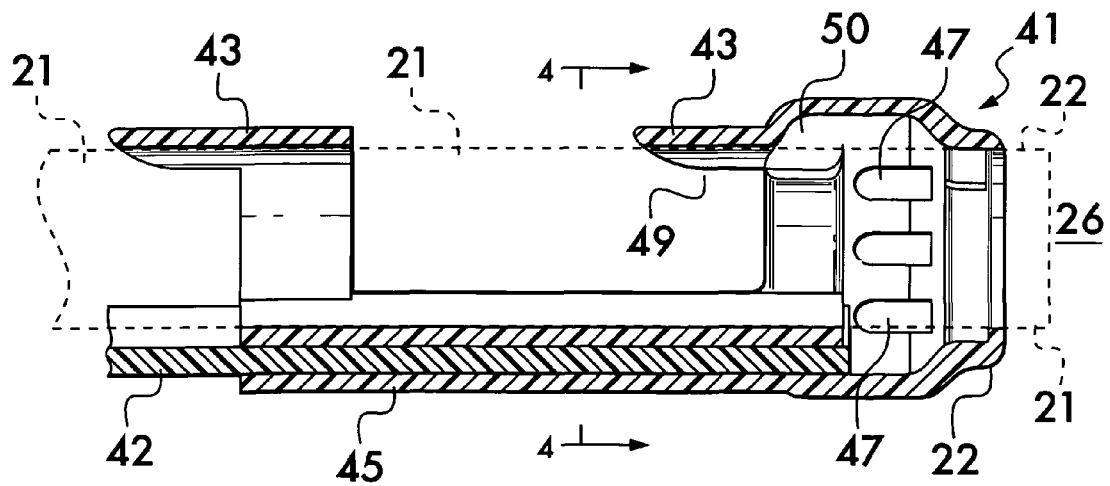
FIG. 3 is a vertical sectional view, taken on line 3-3 of FIG. 2, showing the evacuation chamber secured on the distal end of the endoscope tube.
Figure 4:
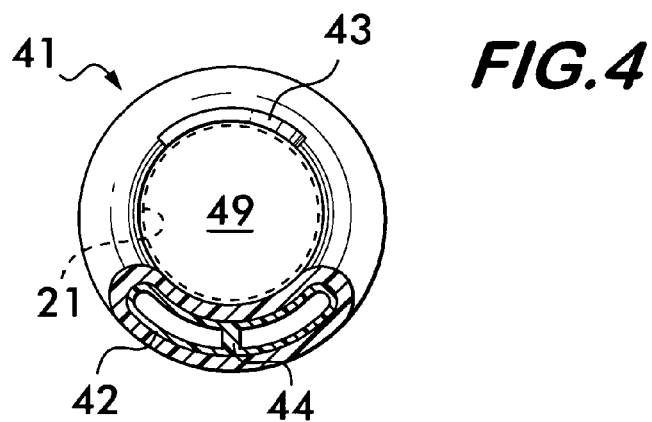
FIG. 4 is a sectional view taken on the line 4-4 of FIG. 3.
Figure 5:
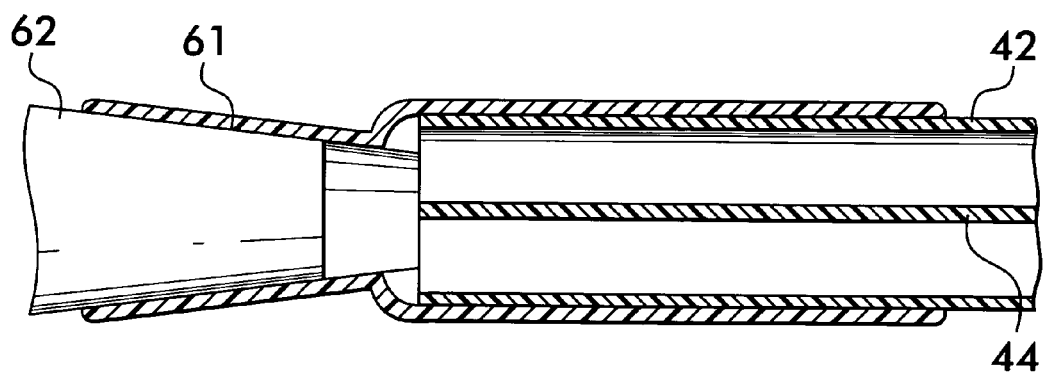
FIG. 5 is a vertical sectional view taken longitudinally through the proximate end of the evacuation tube, showing a connection that secures the evacuation tube to a vacuum pump.

The evacuation chamber 41, as seen, for instance, in FIGS. 2 and 3, is in the general form of a cylinder that fits circumferentially over the distal end 22 of the endoscope tube 21. The generally cylindrically shaped evacuation chamber 41 is further attached to the distal end 22 of the endoscope tube 21, which is shown in phantom in FIGS. 2 and 3, by a band 43, integral with a hollow flat socket 45, that receives flat evacuation tube 42, which is open to evacuation chamber 41. The evacuation chamber 41, band 43, and hollow flat socket 45 are integral with each other and are formed of a soft rubber, or plastic, which permits the evacuation chamber 41 to be stretched and positioned longitudinally along, and elastically held to, the endoscope tube 21 at a location the operator deems optimum. Such optimum location may be as close as ⅛" away from the tip at the distal end 22 of the endoscope tube 21, from which the refrigerant is sprayed at the cold treatment site 26, and the expansion from a liquid to a gas occurs. So positioned, the evacuation chamber 41 does not interfere with the line of sight of the operator conducting the cryospray treatment just beyond such distal end 22 at cold treatment site 26.

The evacuation chamber 41 has radially extending intake ports 47 through which gas from the cold treatment site 26 is suctioned into a cylindrical space 50 formed circumferentially about the endoscope tube 21 near the cold treatment site 26.

The radially extending intake ports 47 extending into the cylindrical space 50 in the interior of the evacuation chamber 41 do not suction the gas longitudinally along the endoscope tube 21 from the cold treatment site at the tip of the distal end 22 of endoscopic tube 21, but rather suction radially of the endoscope tube 21, so there is no interference with the spray exiting longitudinally from the tip at the distal end 22 of the endoscope tube 21 in the cryospray treatment. The cylindrical band 43 extending from a hollow flat socket 45 that is integrally a part of the evacuation chamber 41 further elastically secures the evacuation chamber 41 to the endoscope tube 21. The distal end 22 of endoscope tube 21 fits into the round circular socket 49 of evacuation chamber 41. The radially inward surface of round circular socket 49 conforms to the radial outward surface of endoscope tube 21.

The end of flat evacuation tube 42 fits into the hollow flat socket 45 of the evacuation chamber 41 at the distal end of the endoscope tube 21, and into the vacuum pump 60 at the proximate end of the evacuation tube 21 by a funnel shaped connection 61 that fits over a corresponding shaped connection on vacuum pump inlet 62.

The evacuation tube 42 in cross section is flat, with an interior stiffening web 44 that prevents the extended sides of the evacuation tube 42 from kinking or collapsing and thus terminating the flow of evacuated gases, as could occur in a tube having a circular cross section.

The flat cross section of the evacuation tube 42 also occupies less space adjacent the endoscope tube 21, so that there is less possibility of interference with the placement, operation, and extraction of the endoscope tube 21 and the evacuation tube 42.

In operation, the evacuation chamber 41 on the end of the evacuation tube 42 is fitted over the distal end 22 of the endoscope tube 21, at a distance of, for instance, 1/8" from the tip of endoscope tube 21, where it is held elastically circumferentially, so that it does not slide longitudinally relative to endoscope tube 21. The evacuation tube extends and is connected to the vacuum pump 60.

The operator threads the endoscope tube 21, along with the evacuation tube 42, into the patient to the cold treatment site 26.

As the cryospray is applied at the site, the resultant gases are suctioned into the cylindrical space 50 within evacuation chamber 41 through the radially extending intake ports 47, back into the vacuum pump 60 where they are suitably disposed.

After the treatment, the entire combination of evacuation tube 42, evacuation chamber 41, and endoscope tube 21 is withdrawn.

What is claimed is:

1. In combination with an endoscope (20) and a cryoprobe instrument, extending within a tube (21) of the endoscope (20), that (a) conducts a cryogenic refrigerant to a cold treatment site (26) within the patient, and (b) sprays the cryogenic liquid through a spray nozzle at the cold treatment site (26) to create a cold atmosphere, wherein the cryogenic liquid exiting through the spray nozzle changes from a liquid to a gas, the improvement comprising
a gas evacuation device (40) having:
a. a vacuum source (60) outside the patient;
b. an evacuation tube (42) that is connected to the vacuum source (60) and that extends into the patient along the endoscope tube (21) to the cold treatment site (26) where the cryogenic refrigerant exits from the spray nozzle and changes from a liquid into a gas; and
c. an evacuation chamber (41) elastically secured circumferentially to the endoscope tube (21) near its distal end (22), adjacent the spray nozzle, that has radially extending intake ports (47) in the evacuation chamber (40) adapted to vacuum the gases created at the cold treatment site (26) into a cylindrical space (50) within the evacuation chamber (41) for evacuation through the evacuation tube (42) to outside the patient.

2. The combination of claim 1 wherein the cold atmosphere is created through a Joule-Thompson effect.

3. The combination of claim 1 wherein the cold atmosphere is created by cold liquid nitrogen.

4. The combination of claim 1 wherein the evacuation tube (42) is flat sided, with an interior stiffening web (44) connecting the flat sides.

5. The combination of claim 1, wherein the cylindrical space within the evacuation chamber (41) is partly formed by a segment of the exterior of the endoscope tube (21).

* * * * *